US00PP21936P3

(12) United States Plant Patent
White

(10) Patent No.: US PP21,936 P3
(45) Date of Patent: May 31, 2011

(54) APPLE TREE NAMED 'PREMA153'

(50) Latin Name: ***Malus domestica* Mill.**
Varietal Denomination: PremA153

(75) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 12/584,488

(22) Filed: Sep. 3, 2009

(65) Prior Publication Data

US 2010/0077519 P1 Mar. 25, 2010

Related U.S. Application Data

(60) Provisional application No. 61/191,036, filed on Sep. 4, 2008.

(51) Int. Cl.
*A01H 5/00* (2006.01)

(52) U.S. Cl. ..... Plt./172

(58) Field of Classification Search ..... Plt./172
See application file for complete search history.

*Primary Examiner* — Susan B McCormick Ewoldt
(74) *Attorney, Agent, or Firm* — Ballew Law

(57) ABSTRACT

'PremA153' is a new and distinct apple tree (*Malas domestics* Mill.) notable for its attractive blush yellow color and excellent flavor and texture.

3 Drawing Sheets

Genus and Species:
*Malus domestica* Mill.
Variety denomination:
'PremA153'.

BACKGROUND AND SUMMARY OF THE VARIETY

The new variety of apple tree 'PremA153' was created in the course of a planned breeding program carried out in Hawkes Bay, New Zealand. 'PremA153' originated as a result of a controlled cross of 'Tenroy Gala' (U.S. Plant Pat. No. 4,121), the seed parent, and 'Braebum' (not patented), the pollen parent. 'PremA153' was selected as a single plant from among a population of seedlings derived from the parents, and was selected for its attractive blush yellow fruit and its excellent flavor and texture. Asexual propagation by budding was first carried out in Havelock North, New Zealand. The variety has since been observed over a number of asexually propagated generations, and has been found to remain true to type.

BRIEF DESCRIPTION OF THE PHOTOGRAPHS

Figure 1:
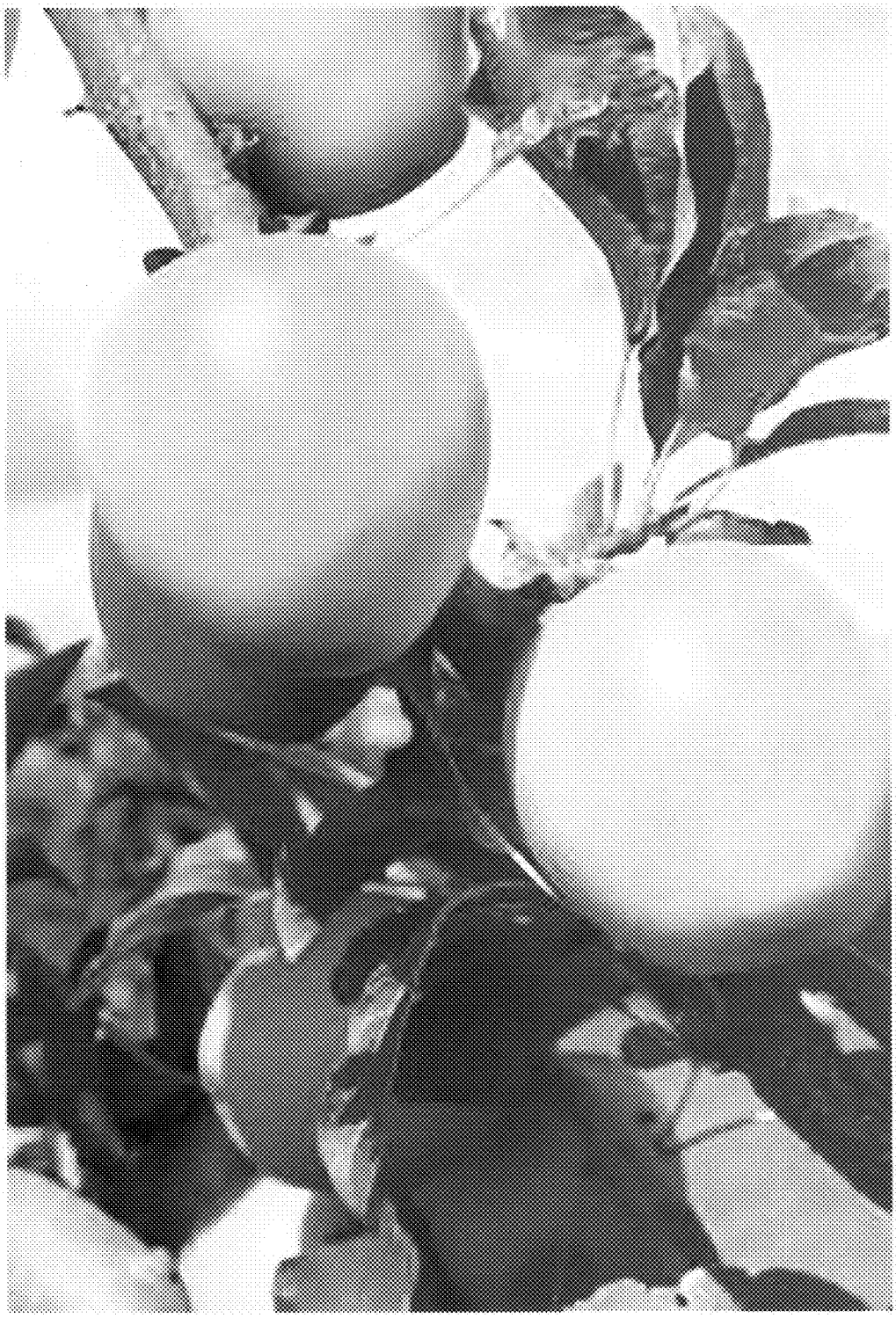
Figure 2:
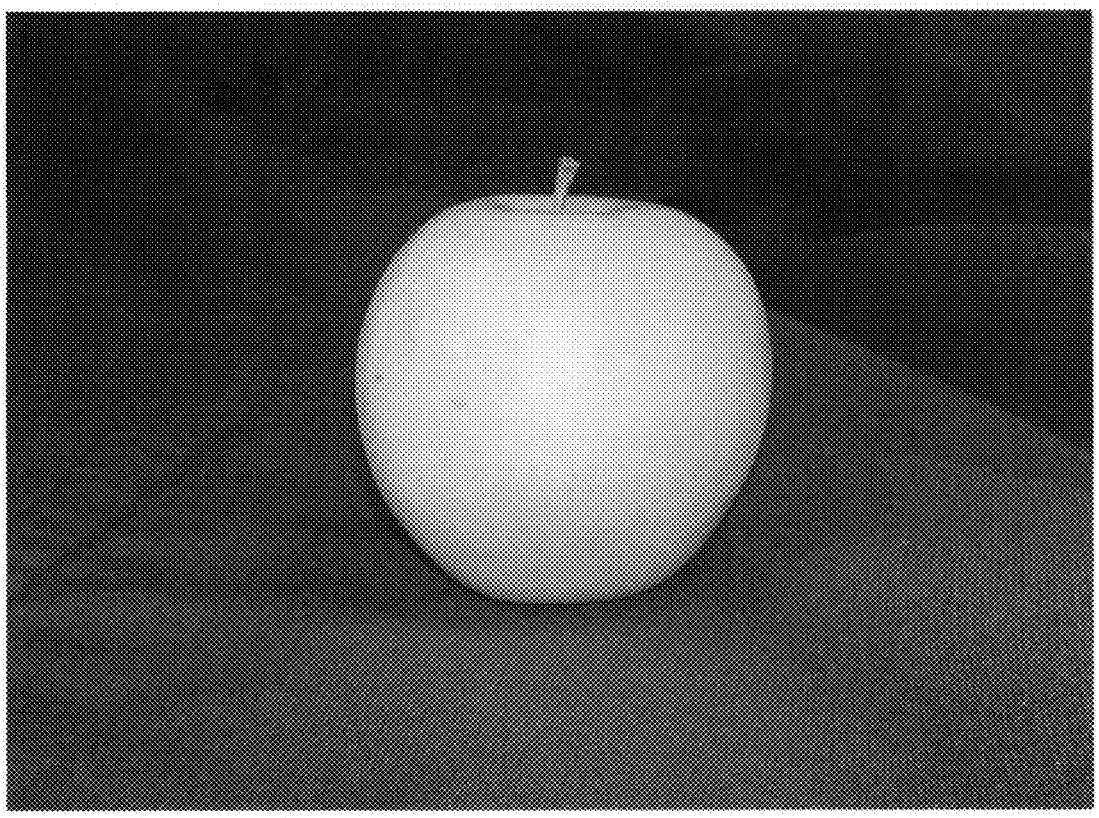
Figure 3:
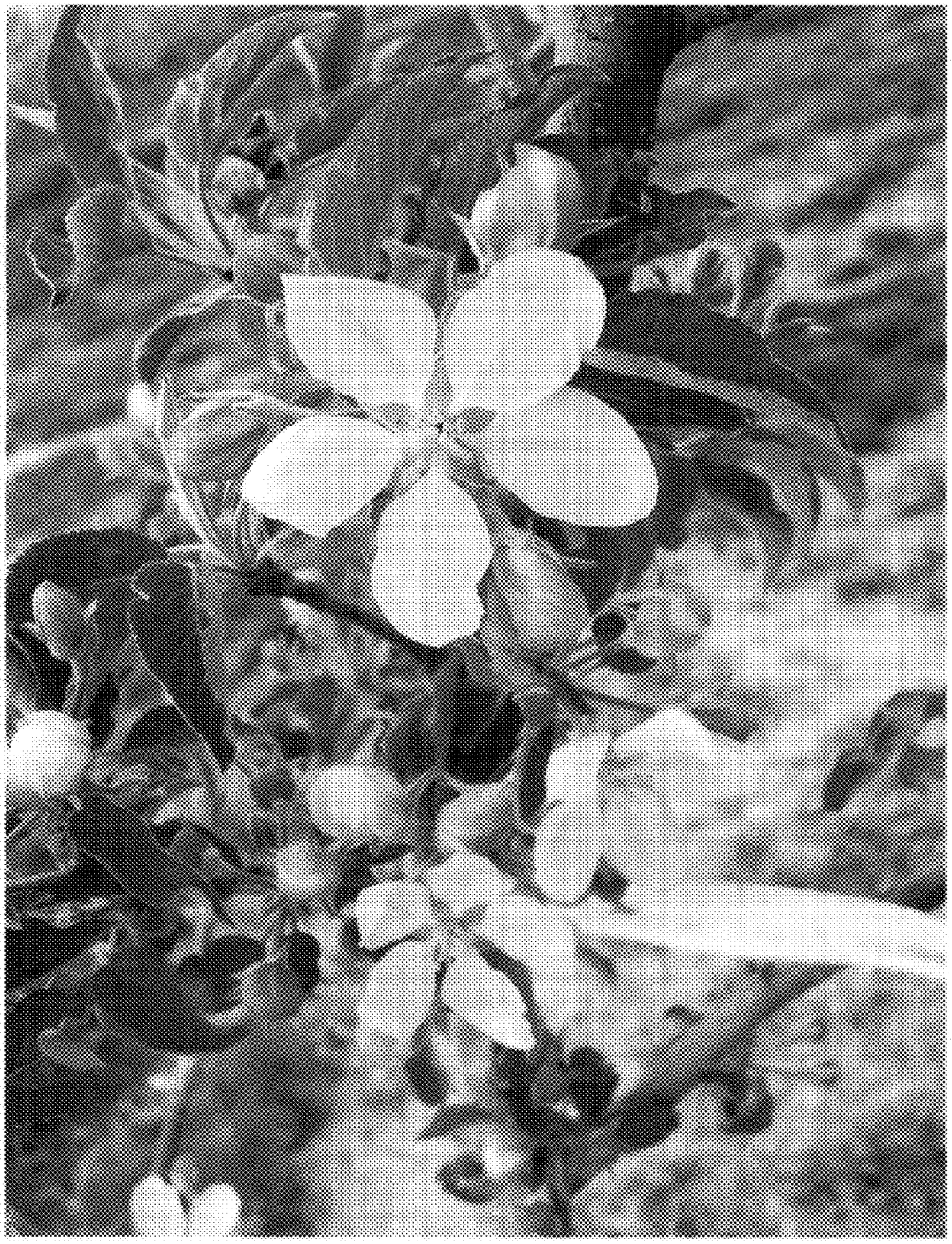

FIG. 1 shows the fruit and leaves of 'PremA153';
FIG. 2 shows the fruit of 'PremA153'; and
FIG. 3 shows the blossoms of 'PremA153.'

DETAILED BOTANICAL DESCRIPTION

The following detailed botanical description is based on observations of two year old 'PremA153' apple trees grown at Parker, Washington. Color descriptions refer to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Vigorous.
- *Habit.*—Semi-Upright.
- *Size.*—Height: 2.0 m; spread 0.7 m.
- *Trunk.*—Diameter: 5.1 cm at 30 cm above graft union; bark texture smooth; color grey-brown 199D.
- *Branches.*—Middle of tree; length 102 cm; diameter 2.5 cm; crotch angle 70°; color grey-brown 199D.
- *Winter hardiness.*—Hardy in area tested.

Dormant one year old shoot:
- *Size.*—Diameter 1.0 cm; length 71 cm.
- *Color.*—Greyed-orange 177A.
- *Internode length.*—3.8 cm.
- *Number of lenticels.*—23 per square inch.

Flowers:
- *Bud.*—Quantity per spur 4 to 5; length 1 cm; diameter 0.5 cm; color red-purple 63B.
- *Flower Color* (*balloon stage*).—Red-purple 68C.
- *Petals.*—Quantity per flower 5; not touching; upper surface color white N155A; lower surface color red-purple 68C when fully open.
- *Flower.*—Diameter 3.5 cm.
- *Sepals.*—Quantity per flower 5; length 0.8cm; width 0.5cm; color yellow-green 144A.
- *Pedicel.*—Length 2.3 cm; diameter 0.1 cm; color yellow-green 144A.
- *Pistil.*—Length 1.1 cm.
- *Anthers.*—Quantity per flower 17; length 1.0 cm; pollen color yellow 12B.
- *Stigma.*—Color 12B.
- *Style.*—Length 0.7; color yellow 12C.
- *Ovary.*—Length 0.5 cm; width 0.2 cm; color yellow-green 144B.
- *Bloom period.*—Late; first bloom Apr. 30, full bloom May 5 at Parker, Washington.
- *Pollination Requirements.*—There are no specific pollination requirements.

Leaf:
- *Size.*—Length 4.0 cm; width 2.3 cm.
- *Margin.*—Serrate.

*Color.*—Upper surface yellow-green 146A; lower surface yellow-green 146A.
*Shape.*—Ovate; apex acuminate; base equilateral.
*Petiole.*—Length 2.6 cm; width 0.1 cm; color yellow-green 144A.

Fruit:

*Size.*—Weight 200 g; diameter 8.5 cm; height 9.0 cm.
*Fruit Shape.*—Globose conical.
*Position of maximum diameter.*—Top.
*Ribbing.*—Absent.
*Crowning at calyx end.*—Present.
*Aperture of eye.*—Closed.
*Size of eye.*—Medium.
*Depth of eye basin.*—Medium.
*Width of eye basin.*—Medium.
*Stalk.*—Diameter 0.2 cm; length 1.7 cm; color greyed-orange 174B.
*Depth of stalk cavity.*—Medium, 1.2 cm.
*Width of stalk cavity.*—Medium 1.5 cm.
*Size of lenticels.*—Small.
*Bloom of skip.*—Present.

Greasiness of skin.—Weak.

*Ground color of skin.*—Yellow 13C.
*Over color of skin.*—Yellow-orange 22A.
*Amount of over color.*—20 percent.
*Pattern of over color.*—Blush.
*Flesh.*—Texture fine; juicy; color white 155A.
*Seeds.*—Quantity per fruit 10; teardrop shape; color brown 200B.
*Aroma.*—Weak.
*Use.*—Fresh Market.

claim

1. I claim a new and distinct apple tree substantially as shown and described herein.

* * * * *